US00PP36883P2

(12) United States Plant Patent
Lee

(10) Patent No.: US PP36,883 P2
(45) Date of Patent: Aug. 12, 2025

(54) ***RHODODENDRON* PLANT NAMED 'ROBLEZP'**

(50) Latin Name: ***Rhododendron* hybrid**
Varietal Denomination: ROBLEZP

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 18/935,736

(22) Filed: Nov. 4, 2024

(51) Int. Cl.
*A01H 5/02* (2018.01)
*A01H 6/36* (2018.01)

(52) U.S. Cl.
USPC ..... Plt./238

(58) Field of Classification Search
USPC ..... Plt./238, 239
See application file for complete search history.

(56) References Cited

PUBLICATIONS https://gardenmediagroup.com/client-news/innovative-horticultural-products-unveiled-at-cultivate-24/ (published Jul. 3, 2024, retrieved online Jan. 7, 2025) (Year: 2024).*
Instagram 'Roblezp' nexus with 'autumn kiss' (Dec. 22, 2024) (Year: 2024).*

* cited by examiner

*Primary Examiner* — Shubo (Joe) Zhou
*Assistant Examiner* — Zachariah Allan Kay
(74) *Attorney, Agent, or Firm* — Cassandra Bright

(57) ABSTRACT

A new and distinct cultivar of *Rhododendron* plant named 'ROBLEZP' is disclosed, characterized by unique pink and white semi-double flowers, blooming intermittently from spring to fall. Plants have a strong root system, superior landscape qualities and are tolerant of pests. The new cultivar is a *Rhododendron*, suitable for ornamental garden purposes.

1 Drawing Sheet

Latin name of the genus and species: *Rhododendron* hybrid.

Variety denomination: 'ROBLEZP'.

BACKGROUND OF THE INVENTION

The new cultivar is a product of a planned breeding program by the inventor to develop new *Rhododendron* varieties with stable bi-colored flowers, repeat blooming, all-around sturdiness, pest resistance and diverse environmental adaptability. The seed and pollen parents were among unnamed, unpatented proprietary Azalea seedlings selected for the desirable traits listed above. The open field hand-pollination resulting in the new cultivar was made during 2010 at a nursery in Independence, Louisiana.

*Rhododendron* 'ROBLEZP' was found and selected in 2016 at the same nursery in Independence, Louisiana. The first asexual propagation occurred in the Fall of 2016 by semi-hardwood cuttings at the same nursery. 'ROBLEZP' has been found to retain its distinctive characteristics through successive asexual propagations over multiple generations.

SUMMARY OF THE INVENTION

The cultivar 'ROBLEZP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROBLEZP'. These characteristics in combination distinguish 'ROBLEZP' as a new and distinct *Rhododendron* cultivar:

1. Semi-double flowers with unique pink and white coloring and petaloid structures.
2. Easy to maintain desired height and width with pruning.
3. Tolerant to environmental stressors.
4. Repeat blooming in spring, summer and fall.

COMPARISON TO PARENT VARIETIES

Parent comparisons are unavailable as the exact parents cannot be identified.

COMMERCIAL COMPARISON

'ROBLEZP' can be compared to the commercial variety *Rhododendron* 'ROBLET' U.S. Plant Pat. No. 25,072. Plants of the new cultivar 'ROBLEZP' are similar to plants of 'ROBLET' in most horticultural characteristics. Plants of the new cultivar 'ROBLEZP', however, differ in the following:

1. Flower color of 'ROBLEZP' is pink and white; flower color of 'ROBLET' is coral and white.
2. Plants of 'ROBLEZP' are more compact than plants of 'ROBLET'.

BRIEF DESCRIPTION OF THE PHOTOGRAPHS

'ROBLEZP' is illustrated in the accompanying photograph, which shows the flowering plant of 'ROBLEZP' in a two-gallon container at approximately 2-years old. The colors shown are as true as can be reasonably obtained by conventional photographic procedures. Colors in the photograph may differ slightly from the color values cited in the detailed botanical description, which accurately describes the new hybrid *Rhododendron.*

DETAILED BOTANICAL DESCRIPTION

The following is a detailed description of the botanical characteristics of the new and distinct *Rhododendron* 'ROBLEZP'. The detailed description was taken of a 2-year-old plant in a 2-gallon container grown outdoors in Loxley, AL in 2024. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Botanical classification: *Rhododendron* hybrid 'ROBLEZP'.

ROOT

Typical method: Semi-hardwood cuttings.

Root description: Fine, fibrous young roots, well branched. Colored near RHS Grey-Brown 199A.

PLANT

Plant type: Flowering shrub.

Growth habit: Spreading, low growing.

Height: Approximately 45 cm to top of foliar and flowering plane.

Width: Approximately 75 cm.

Growth rate: Moderate

Vigor: Good.

Branching characteristics: Moderately well-branched, average 5 to 7 primary branches from the center of the plant. Branches occur at approximately 60° to 75° angles.

Length of primary branches: Average range 15 to 35 cm.

Diameter of primary branches: Average range 6 to 9 mm.

Primary branch strength: Very strong, difficult to break.

Primary branch color:

- *Young branches.*—Near RHS Yellow-Green 153B covered in Greyed-Orange 172A.
- *Woody branches.*—Near RHS Brown 200D, streaked Grey-Green 197B.

Primary branch texture:

- *Immature growth.*—Hirsute.
- *Older growth.*—Scaly.

Lateral branches:

Number of lateral branches: Approximately 2 to 6 per primary branch.

Length of lateral branches: Average 8 to 22 cm.

Diameter of lateral branches: Average 6 mm.

Lateral branch strength: Very strong, flexible.

Lateral branch color: Immature branches near RHS Yellow-Green N144B, lightly flushed Greyed-Red 178C.

Lateral branch texture: Hirsute.

Internode length: Average range 2 to 4 cm.

FOLIAGE

Leaf:

- *Type.*—Simple.
- *Arrangement.*—Alternate.
- *Length.*—Approximately 4.5 cm.
- *Width.*—Approximately 2.5 cm.
- *Shape.*—Obovate.
- *Apex.*—Broadly rounded with very small mucronate tip.
- *Base.*—Broad attenuate.
- *Attachment.*—Stalked.
- *Margin.*—Entire.
- *Texture of top surface.*—Pubescent. Hairs appressed.
- *Texture of bottom surface.*—Pubescent. Most hairs present along main vein and margin.
- *Color.*—Young foliage upper side: Near RHS Green 137B. Young foliage under side: Near RHS Green 137D. Mature foliage upper side: Near RHS Green 139A. Mature foliage under side: Near RHS Green 137C.
- *Venation.*—Type: Pinnate. Venation color upper side: Near RHS Yellow-Green 145A. Venation color under side: Near RHS Yellow-Green 144C.
- *Petiole.*—Length: About 1 to 3 mm. Diameter: About 2 mm. Color: Upper Surface: Near RHS Yellow-Green 146D. Lower Surface: Near RHS Yellow-Green N144A. Texture of top surface: Pubescent. Hairs appressed. Texture of bottom surface: Pubescent. Hairs appressed.

FLOWER

Natural flowering season: Intermittently from early Spring through Fall.

Arrangement: Axillary clusters of perfect, double open funnel shaped individual flowers. Typically 5 to 7 flowers per cluster.

Inflorescence:

- *Height.*—Average 8 cm.
- *Diameter.*—Average 12 to 16 cm.

Peduncle:

- *Length.*—Average 2 cm.
- *Diameter.*—3 mm.
- *Color.*—Near RHS Yellow-Green N144A.
- *Texture.*—Hirsute.
- *Aspect.*—Straight. Angle of attachment, approximately 25° angle from stem.

Pedicel:

- *Length.*—Average 1.1 to 1.4 cm.
- *Diameter.*—3 mm.
- *Color.*—Near RHS Yellow-Green 145A, flushed Red-Purple 61C near attachment to flower.
- *Texture.*—Densely pubescent.
- *Aspect.*—Straight. Approximately 45° angle from stem.

Flowers:

- *Length.*—Average 4.5 cm.
- *Diameter.*—Average 6 cm.
- *Aspect.*—Outward facing.
- *Persistence.*—Self-cleaning.
- *Fragrance.*—Very faint, leafy scent.

Tube:

- *Length.*—Average 15 mm.
- *Width a widest point.*—Approximately 1.3 cm.
- *Width and narrowest point.*—Approximately 6 mm.

Petals:

*Quantity.*—6 outer petals surrounding 5 to 6 inner petaloids.

*Unfused petal segments.*—Length: Approximately 3 cm. Width: Approximately 2.7 cm.

*Apex.*—Blunt, rounded with shallow (1 to 3 mm), irregular lobes or notches.

*Shape.*—Unfused portion, obovate.

*Margin.*—Entire. Ruffled.

*Arrangement.*—Overlapping, bilateral symmetry dissecting bottom petal. Petals fused approximately ⅓ fused from base.

*Texture.*—Smooth, all surfaces.

*Color.*—Upper surface at first opening: Large basal section near RHS Red-Purple 62D, center 62C, thick margin N57D. Under surface at first opening: Large basal section near RHS Red-Purple 62D, center 62C, thick margin N57D. Large basal section near RHS Red-Purple Inner surface at maturity: 62D, center 62C, thick margin 63B. Large basal section near RHS Red-Purple 7 Outer surface at maturity: 62D, center 62C, thick margin 63A. Large basal section near RHS Red-Purple 9 Upper surface at fading: 65D, center 70D, thick margin 67B A. Under surface at fading: Large basal section near RHS Red-Purple 65D, center 70D, thick margin 67B.

Petaloids:

*Quantity.*—5 to 6.

*Length.*—Approximately 4.0 cm.

*Width.*—Approximately 1.8 cm.

*Base.*—Fused.

*Apex.*—Blunt, rounded with shallow (1 to 3 mm), irregular lobes or notches.

*Shape.*—Unfused portion, irregular obovate.

*Margin.*—Entire, ruffled.

*Arrangement.*—Overlapping, bilateral symmetry dissecting bottom petal. Petals fused approximately ⅓ fused from base.

*Texture.*—Smooth all surfaces.

*Color.*—Upper surface at first opening: Large basal section near RHS Red-Purple 62D, center 62C, thick margin N57D. Under surface at first opening: Large basal section near RHS Red-Purple 62D, center 62C, thick margin N57D. Inner surface at maturity: Large basal section near RHS Red-Purple 62D, center 62C, thick margin 63B. Outer surface at maturity: Large basal section near RHS Red-Purple 62D, center 62C, thick margin 63A. Upper surface at fading: Large basal section near RHS Red-Purple 65D, center 70D, thick margin 67B. Under surface at fading: Large basal section near RHS Red-Purple 65D, center 70D, thick margin 67B.

Bud:

*Shape.*—Elliptic.

*Length.*—2.5 cm.

*Diameter.*—1.2 cm.

*Color.*—Near RHS Red-Purple 62D, striped N57D.

Sepals:

*Quantity per flower.*—5.

*Shape.*—Narrow deltate.

*Length.*—10 mm.

*Width.*—4 mm.

*Apex.*—Acute.

*Base.*—Fused.

*Margin.*—Entire.

*Texture.*—Highly pubescent.

*Color.*—Inner Surface: Near RHS Yellow-Green 145A. Outer Surface: Near RHS Yellow-Green 145B.

REPRODUCTIVE ORGANS

Stamens:

*Number.*—4 or 5.

*Length.*—Entirely fused to petaloids, only anther separate.

*Filament color.*—RHS Red-Purple N57C upper ⅕ N66B.

*Protrusion.*—Slightly protruding.

*Anthers.*—Length: Approximately 1 mm. Color: Near RHS Red-Purple 59A. Pollen: Not observed.

Pistil:

*Number.*—1.

*Length.*—5 cm.

*Style.*—Length: Average 4.5 cm. Color: Lower half near RHS Red-Purple 62C; upper half near Red-Purple 57A.

*Stigma.*—Shape: Globular. Color: Near RHS Red-Purple N57A.

*Ovary.*—Length: 5 mm. Diameter: Approximately 5 mm. Texture: Sericeous. Color: Near RHS Yellow-Green 144C.

OTHER CHARACTERISTICS

Fruit and seed: Not observed.

Disease and pest resistance: Field observations show tolerance to typical pests of *Rhododendron*, which include lace wings and red mites. The new cultivar did not show susceptibility to root diseases observed in other cultivars in the same field test.

Temperature tolerance: Tolerant to USDA Zone 6.

What is claimed is:

1. A new and distinct cultivar of *Rhododendron* plant named 'Roblezp' as herein illustrated and described.

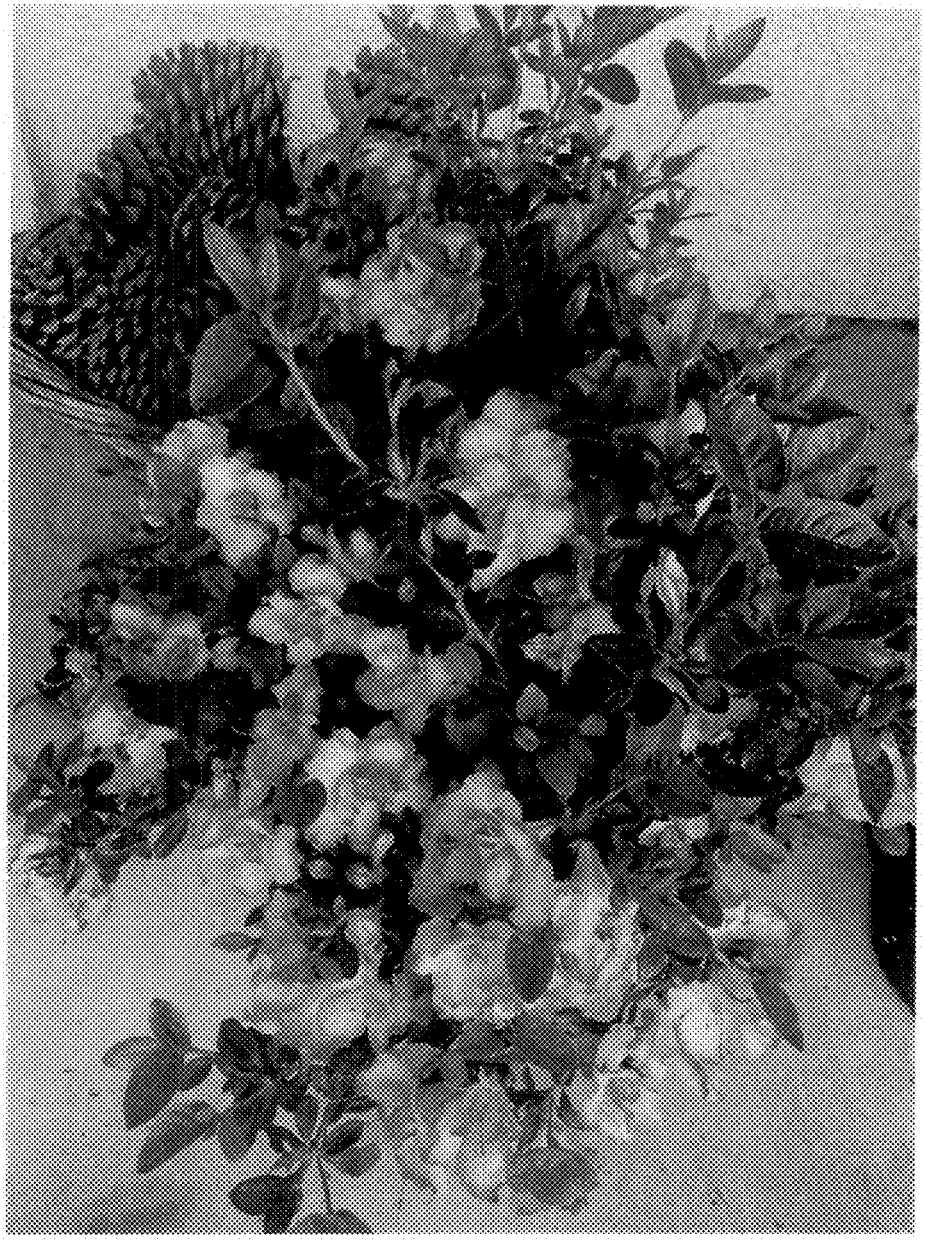

* * * * *